(12) United States Patent
Fallin et al.

(10) Patent No.: US 10,898,211 B2
(45) Date of Patent: Jan. 26, 2021

(54) OPENING AND CLOSING WEDGE OSTEOTOMY GUIDE AND METHOD

(71) Applicant: Crossroads Extremity Systems, LLC, Memphis, TN (US)

(72) Inventors: T. Wade Fallin, Hyde Park, UT (US); Daniel J. Triplett, Providence, UT (US); Robert W. Hoy, Essex Junction, VT (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 1096 days.

(21) Appl. No.: 14/994,362

(22) Filed: Jan. 13, 2016

(65) Prior Publication Data

US 2016/0199076 A1   Jul. 14, 2016

Related U.S. Application Data

(60) Provisional application No. 62/103,397, filed on Jan. 14, 2015.

(51) Int. Cl.
| | | |
|---|---|---|
| *A61B 17/17* | (2006.01) | |
| *A61B 17/15* | (2006.01) | |
| *A61B 17/58* | (2006.01) | |
| *A61F 2/46* | (2006.01) | |
| *A61B 17/80* | (2006.01) | |

(52) U.S. Cl.
CPC ........ *A61B 17/1739* (2013.01); *A61B 17/152* (2013.01); *A61B 17/8061* (2013.01)

(58) Field of Classification Search
CPC ............ A61B 17/1739; A61B 17/1682; A61B 17/8061; A61B 17/846; A61B 17/86; A61B 17/152

USPC ............ 606/96–98, 87–89, 70–71, 280–299
See application file for complete search history.

(56) References Cited

U.S. PATENT DOCUMENTS

| 4,069,824 A | 1/1978 | Weinstock |
| 4,335,715 A | 6/1982 | Kirkley |
| 4,349,018 A | 9/1982 | Chambers |
| 4,409,973 A | 10/1983 | Neufeld |

(Continued)

FOREIGN PATENT DOCUMENTS

| EP | 570187 A1 | 11/1993 |
| EP | 570187 B1 | 7/1996 |

(Continued)

OTHER PUBLICATIONS

The Next Generation in Foot & Ankle Repair and Reconstruction Technology, Arthrex, Inc., www.arthrex.com, 2016, 76 pp.

(Continued)

*Primary Examiner* — Jessica Weiss
(74) *Attorney, Agent, or Firm* — Knobbe Martens Olson & Bear LLP

(57) ABSTRACT

Methods and devices for performing an osteotomy on a bone are presented. In one example of the invention, a method of performing an osteotomy on a bone includes removing a portion of bone from a first side of the bone to create a gap on the first side of the bone; making a cut on a second side of the bone, opposite the first side; and rotating the bone from a first position to a second position to close the gap on the first side of the bone and open the cut on the second side of the bone to create a gap on the second side of the bone.

17 Claims, 16 Drawing Sheets

(56) References Cited

U.S. PATENT DOCUMENTS

| | | | | |
|---|---|---|---|---|
| 4,440,168 | A | 4/1984 | Warren | |
| 4,501,268 | A | 2/1985 | Comparetto | |
| 4,502,474 | A | 3/1985 | Comparetto | |
| 4,509,511 | A | 4/1985 | Neufeld | |
| 4,565,191 | A | 1/1986 | Slocum | |
| 4,627,425 | A | 12/1986 | Reese | |
| 4,632,102 | A | 12/1986 | Comparetto | |
| 4,664,102 | A | 5/1987 | Comparetto | |
| 4,708,133 | A | 11/1987 | Comparetto | |
| 4,750,481 | A | 6/1988 | Reese | |
| 4,757,810 | A | 7/1988 | Reese | |
| 4,852,558 | A * | 8/1989 | Outerbridge | A61B 17/0642 606/75 |
| 4,913,144 | A * | 4/1990 | Del Medico | A61B 17/0642 411/450 |
| 4,952,214 | A | 8/1990 | Comparetto | |
| 5,035,698 | A | 7/1991 | Comparetto | |
| 5,042,983 | A | 8/1991 | Rayhack | |
| 5,049,149 | A | 9/1991 | Schmidt | |
| 5,053,039 | A * | 10/1991 | Hofmann | A61B 17/15 606/86 R |
| 5,078,719 | A | 1/1992 | Schreiber | |
| 5,112,334 | A | 5/1992 | Alchermes | |
| 5,147,364 | A | 9/1992 | Comparetto | |
| 5,176,685 | A | 1/1993 | Rayhack | |
| 5,246,444 | A * | 9/1993 | Schreiber | A61B 17/152 606/87 |
| 5,413,579 | A * | 5/1995 | Tom Du Toit | A61B 17/15 606/87 |
| 5,449,360 | A | 9/1995 | Schreiber | |
| 5,470,335 | A | 11/1995 | Du Toit | |
| 5,540,695 | A | 7/1996 | Levy | |
| 5,578,038 | A | 11/1996 | Slocum | |
| 5,601,565 | A | 2/1997 | Huebner | |
| 5,613,969 | A | 3/1997 | Jenkins, Jr. | |
| 5,620,448 | A | 4/1997 | Paddu | |
| 5,643,270 | A | 7/1997 | Combs | |
| 5,667,510 | A | 9/1997 | Combs | |
| H1706 | H * | 1/1998 | Mason | 606/87 |
| 5,722,978 | A | 3/1998 | Jenkins | |
| 5,749,875 | A | 5/1998 | Paddu | |
| 5,779,709 | A | 7/1998 | Harris, Jr. | |
| 5,843,085 | A * | 12/1998 | Graser | A61B 17/15 606/87 |
| 5,911,724 | A | 6/1999 | Wehrli | |
| 5,980,526 | A | 11/1999 | Johnson | |
| 5,984,931 | A | 11/1999 | Greenfield | |
| 6,007,535 | A | 12/1999 | Rayhack | |
| 6,027,504 | A * | 2/2000 | McGuire | A61B 17/0206 128/898 |
| 6,030,391 | A | 2/2000 | Brainard | |
| 6,203,545 | B1 | 3/2001 | Stoffella | |
| 6,248,109 | B1 | 6/2001 | Stoffella | |
| 6,391,031 | B1 * | 5/2002 | Toomey | A61B 17/15 606/82 |
| 6,547,793 | B1 | 4/2003 | McGuire | |
| 6,676,662 | B1 | 1/2004 | Bagga | |
| 6,755,838 | B2 | 6/2004 | Trnka | |
| 6,796,986 | B2 | 9/2004 | Duffner | |
| 7,018,383 | B2 | 3/2006 | McGuire | |
| 7,112,204 | B2 | 9/2006 | Justin | |
| 7,182,766 | B1 | 2/2007 | Mogul | |
| 7,540,874 | B2 | 6/2009 | Trumble | |
| 7,572,258 | B2 | 8/2009 | Stiernborg | |
| 7,691,108 | B2 | 4/2010 | Lavallee | |
| 7,763,026 | B2 | 7/2010 | Egger | |
| 7,967,823 | B2 | 6/2011 | Ammann | |
| 7,972,338 | B2 * | 7/2011 | O'Brien | A61B 17/152 606/87 |
| 8,062,301 | B2 | 11/2011 | Ammann | |
| 8,083,746 | B2 | 12/2011 | Novak | |
| 8,137,406 | B2 | 3/2012 | Novak | |
| 8,236,000 | B2 | 8/2012 | Ammann | |
| 8,262,664 | B2 | 9/2012 | Justin | |
| 8,277,459 | B2 | 10/2012 | Sand | |
| 8,282,645 | B2 * | 10/2012 | Lawrence | A61B 17/15 606/87 |
| 8,409,209 | B2 | 4/2013 | Ammann | |
| 8,496,662 | B2 | 7/2013 | Novak | |
| 8,529,571 | B2 | 9/2013 | Horan | |
| 8,540,777 | B2 | 9/2013 | Ammann | |
| 8,652,142 | B2 | 2/2014 | Geissler | |
| 8,657,820 | B2 | 2/2014 | Kubiak | |
| 8,702,715 | B2 | 4/2014 | Ammann | |
| 8,771,279 | B2 | 7/2014 | Philippon | |
| 8,777,948 | B2 | 7/2014 | Bernsteiner | |
| 8,888,785 | B2 | 11/2014 | Ammann | |
| 8,900,247 | B2 | 12/2014 | Tseng | |
| 8,906,026 | B2 | 12/2014 | Ammann | |
| 9,113,920 | B2 | 8/2015 | Amman | |
| 9,622,805 | B2 * | 4/2017 | Santrock | A61B 17/1728 |
| 9,687,250 | B2 * | 6/2017 | Dayton | A61B 17/15 |
| 10,292,713 | B2 * | 5/2019 | Fallin | A61B 17/151 |
| 2002/0165552 | A1 | 11/2002 | Duffner | |
| 2004/0097946 | A1 | 5/2004 | Dietzel | |
| 2004/0138669 | A1 | 7/2004 | Horn | |
| 2005/0070909 | A1 | 3/2005 | Egger | |
| 2005/0149042 | A1 * | 7/2005 | Metzger | A61B 17/155 606/88 |
| 2005/0251147 | A1 * | 11/2005 | Novak | A61B 17/15 606/87 |
| 2005/0273112 | A1 | 12/2005 | McNamara | |
| 2006/0129163 | A1 | 6/2006 | McGuire | |
| 2006/0264961 | A1 | 11/2006 | Murray | |
| 2007/0010818 | A1 | 1/2007 | Stone | |
| 2007/0265634 | A1 * | 11/2007 | Weinstein | A61B 17/15 606/87 |
| 2007/0276383 | A1 | 11/2007 | Rayhack | |
| 2008/0015603 | A1 * | 1/2008 | Collazo | A61B 17/152 606/87 |
| 2008/0039850 | A1 | 2/2008 | Rowley | |
| 2008/0147073 | A1 | 2/2008 | Ammann | |
| 2008/0269908 | A1 | 10/2008 | Warburton | |
| 2009/0036931 | A1 | 2/2009 | Pech | |
| 2009/0054899 | A1 | 2/2009 | Ammann | |
| 2009/0210010 | A1 * | 8/2009 | Strnad | A61B 17/8014 606/280 |
| 2009/0222047 | A1 | 9/2009 | Graham | |
| 2010/0130981 | A1 | 5/2010 | Richards | |
| 2010/0152782 | A1 * | 6/2010 | Stone | A61B 17/151 606/280 |
| 2011/0213376 | A1 * | 9/2011 | Maxson | A61B 17/151 606/88 |
| 2011/0188550 | A1 | 11/2011 | Orbay | |
| 2012/0185056 | A1 | 7/2012 | Warburton | |
| 2012/0191199 | A1 | 7/2012 | Raemisch | |
| 2013/0012949 | A1 * | 1/2013 | Fallin | A61B 17/151 606/87 |
| 2013/0226248 | A1 | 8/2013 | Hatch | |
| 2013/0226252 | A1 | 8/2013 | Mayer | |
| 2013/0331845 | A1 | 12/2013 | Horan | |
| 2014/0188139 | A1 * | 7/2014 | Fallin | A61B 17/0491 606/145 |
| 2014/0194999 | A1 | 7/2014 | Orbay | |
| 2014/0343555 | A1 | 11/2014 | Russi | |
| 2015/0057667 | A1 | 2/2015 | Ammann | |
| 2015/0245858 | A1 | 4/2015 | Ammann | |
| 2016/0015426 | A1 | 1/2016 | Dayton | |
| 2016/0324532 | A1 | 11/2016 | Montoya et al. | |
| 2017/0042598 | A1 | 2/2017 | Santrock et al. | |
| 2017/0042599 | A1 | 2/2017 | Bays et al. | |

FOREIGN PATENT DOCUMENTS

| | | |
|---|---|---|
| WO | 2000006036 A1 | 2/2000 |
| WO | 2004075775 A1 | 9/2003 |
| WO | 2004089227 A2 | 10/2004 |
| WO | 2005041785 A1 | 5/2005 |
| WO | 2007008348 A2 | 1/2007 |
| WO | 2008097781 A1 | 8/2008 |
| WO | 2016134154 A1 | 8/2016 |
| WO | 2016134160 A1 | 8/2016 |

(56) References Cited

FOREIGN PATENT DOCUMENTS

OTHER PUBLICATIONS

Scarf Osteotomy Technical Information Sheet, TALUS group of GECO, www.geco-medical.org, 2004, 2 pp.
Comprehensive Solutions for Forefoot and Midfoot Surgery using the Mini TightRope System, Arthrex, Inc., www.arthrex.com, 2012, 15 pp.
Distal Extremities Orthopaedic Update, Arthrex, Inc., www.arthrex.com, 2014, 24 pp.
Arthrex Hallux Valgus Solutions, Arthrex, Inc., www.arthrex.com 2009, 2 pp.
The Next Generation in Foot & Ankle Repair and Reconstructions Technology, Arthrex, Inc., www.arthrex.com, 72 pp.
Foot & Ankle Repair and Reconstruction Technology, Arthrex GmbH, www.arthrex.com, 2016, 86 pp.
Comprehensive Solutions for Forefoot and Midfoot Surgery using the Mini TightRope System, Arthrex, Inc., www.arthrex.com 2012, 15 pp.
Shurnas, Paul S., M.D., et al., Proximal Metatarsal Opening Wedge Osteotomy: PMOW—Arthrex LPS System, Arthrex, Inc., www.arthrex.com, 2008, 1 pp.
Speed Triad Medial Technique, BioMedical Enterprises, www.bmetx.com, 2015, 2 pp.
Accu-Cut Osteotomy Guide System, BioPro Implants, www.bioproimplants.com, Brochure No. 17136, Rev4, 2 pp.
The Accu-Cut Osteotomy Guide System, BioPro Implants, www.bioproimplants.com, Brochure No. 16932 Rev07, 2 pp.
Dobbe, et al., "Computer-Assisted and Patient-Specific 3-D Planning and Evaluation of a Single-Cut Rotational Osteotomy for Complex Long-Bone Deformities", Med Biol Eng Comput (2011) 49:1363-1370.
Gregg, Julie, et al., "Plantar Plate Repair and Weil Osteotomy for Meteatarsophalangeal Joint Instability", Foot and Ankle Surgery 13(2007) 116-121.
Meyer, D.C., et al., "A New Methodology for the Planning of Single-Cut Corrective Osteotomies of Mal-Aligned Long Bones", Clinical Biomechanics 20(2005) 223-227.
Oscillating Saw Attachment for EPD/APD, Colibri II and Small Electric Drive, Synthes GmbH, www.synthes.com, 2012, 2 pp.
Weil, Lowell Jr., et al., "Anatomic Plantar Plate Repair Using the Weil Metatarsal Osteotomy Approach", Foot & Ankle Specialist, http://fas.sagepub.com/, 2011, 7 pp.

\* cited by examiner

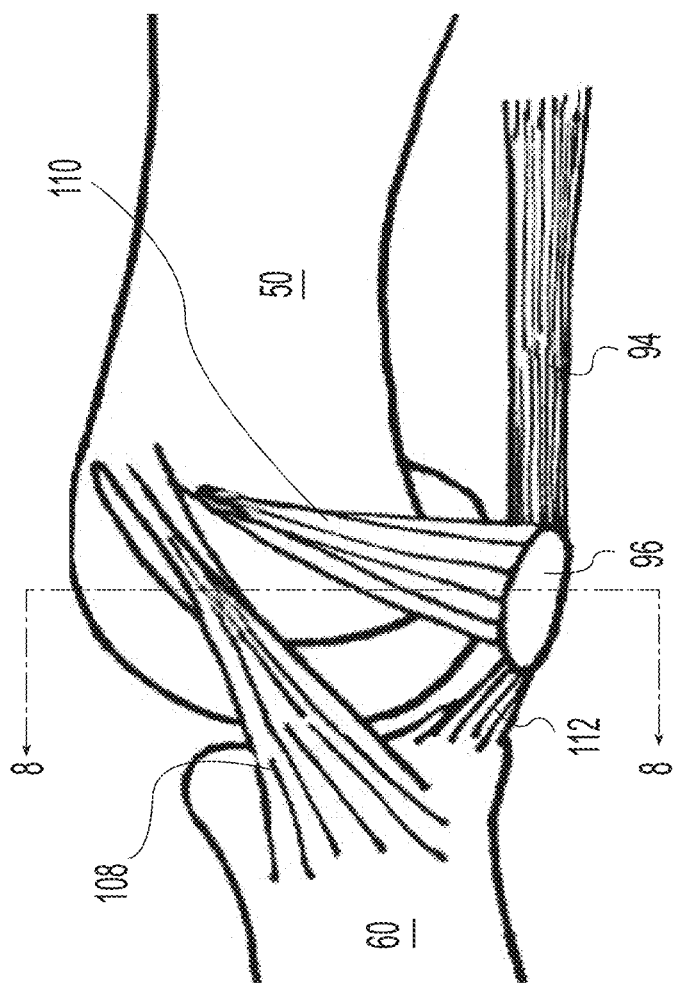
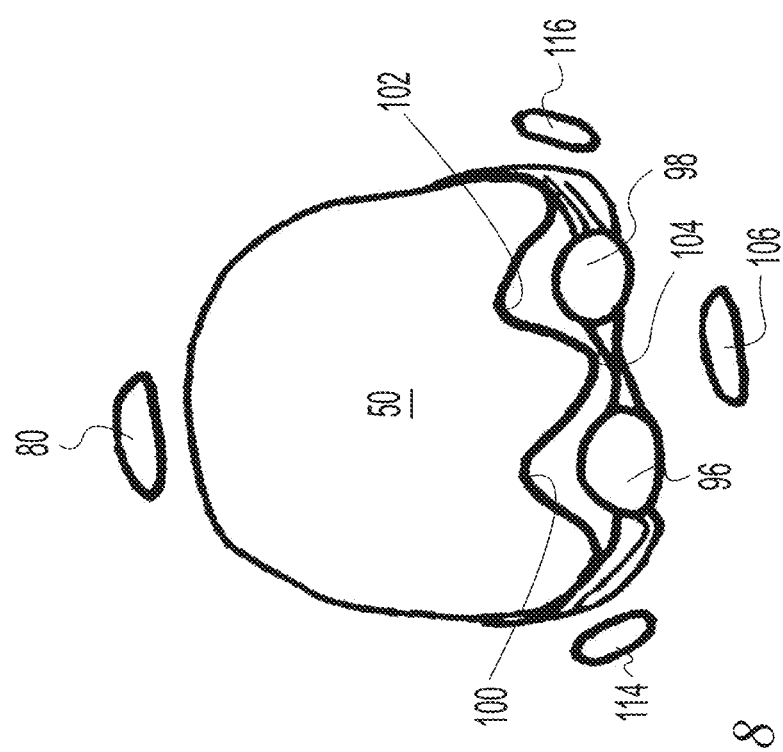
Fig. 7
Fig. 8

OPENING AND CLOSING WEDGE OSTEOTOMY GUIDE AND METHOD

CROSS REFERENCE TO RELATED PATENT APPLICATIONS

This application claims the benefit of U.S. Provisional Application No. 62/103,397, filed Jan. 14, 2015, herein incorporated by reference.

FIELD OF THE INVENTION

The invention relates to methods, implants, and instruments for performing an osteotomy on a bone.

BACKGROUND

Various conditions may affect skeletal joints such as the deterioration, elongation, shortening, or rupture of soft tissues, cartilage, and/or bone associated with the joint and consequent laxity, pain, and/or deformity. It is often desirable to change the angular alignment of a bone or a portion of a bone to restore function and/or reduce pain. To this end, various osteotomy procedures and instruments have been proposed. For example, osteotomies have been performed throughout the body to make various angular adjustments such as in a tibia, fibula, femur, pelvis, humerus, ulna, radius, metacarpal, metatarsal, and other bones. Prior osteotomies couple angular correction and change in bone length in ways that often produce undesirable results.

SUMMARY

The present invention provides methods, implants, and instruments for performing an osteotomy on a bone.

In one example of the invention, a method of performing an osteotomy on a bone includes removing a portion of bone from a first side of the bone to create a gap on the first side of the bone; making a cut on a second side of the bone, opposite the first side; and rotating the bone from a first position to a second position to close the gap on the first side of the bone and open the cut on the second side of the bone to create a gap on the second side of the bone.

In another example of the invention, a method of performing an osteotomy on a metatarsus of a first ray of the human foot includes positioning an osteotomy guide adjacent the metatarsus; guiding a cutter to remove a portion of bone from a first side of the metatarsus to create a gap on the first side of the metatarsus; guiding a cutter to make a cut on a second side of the metatarsus, opposite the first side; rotating the metatarsus from a first position to a second position to close the gap on the first side of the metatarsus and open the cut on the second side of the metatarsus to create a gap on the second side of the metatarsus; and filling the gap created on the second side of the metatarsus.

In another example of the invention, an osteotomy guide includes a guide body having a proximal end, a distal end, and first and second sides. The first side includes first and second guide surfaces that converge from the first side toward the second side. The first and second guide surfaces are operable to guide a cutter to remove a wedge of bone from a first side of a bone. The second side includes a third guide surface extending toward but stopping short of the first and second guide surfaces. The third guide surface being operable to guide a cutter to make a cut on a second side of a bone.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 7 is a medial view of the MTP joint of the first ray of the foot;

FIG. 8 is a sectional view taken along line 8-8 of FIG. 7;

DESCRIPTION OF THE ILLUSTRATIVE EXAMPLES

The following illustrative examples describe implants, instruments and techniques for performing an osteotomy on a bone. The present invention may be used to perform osteotomies on any bone including but not limited to a tibia, fibula, femur, pelvis, humerus, ulna, radius, metacarpal, and metatarsal. However, for convenience, the invention will be illustrated with reference to a metatarsal bone of the first ray of a human foot.

Figure 1:
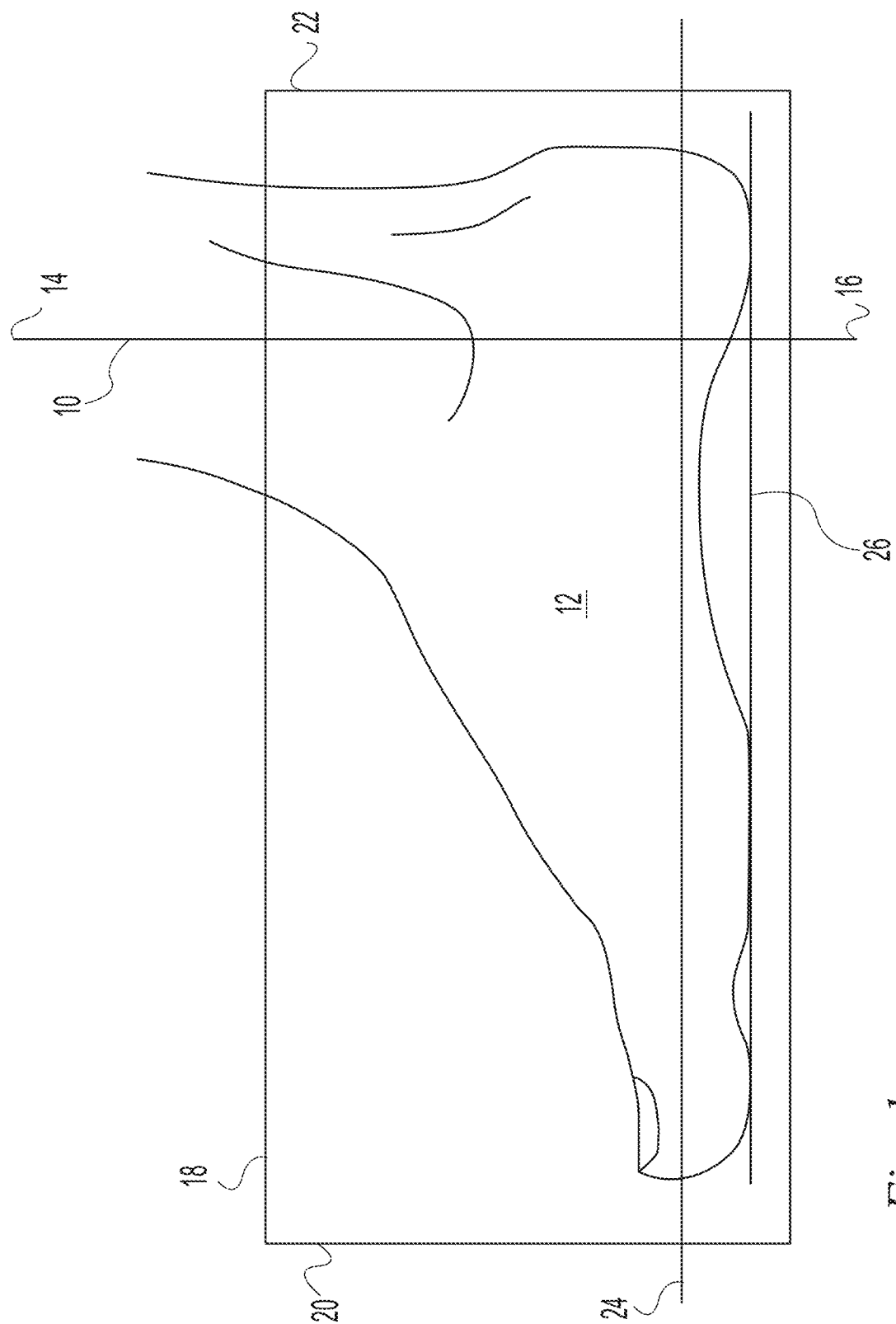
FIG. 1 is side elevation view of a foot illustrating anatomic reference planes and relative directions.

FIG. 1 illustrates the orientation of anatomic planes and relative directional terms that are used for reference in this application. The coronal plane 10 extends from medial 12 (toward the midline of the body) to lateral (away from the midline of the body) and from dorsal 14 (toward the top of the foot) to plantar 16 (toward the sole of the foot). The sagittal plane 18 extends from anterior 20 (toward the front of the body) to posterior 22 (toward the back of the body) and from dorsal 14 to plantar 16. The transverse plane 24 extends anterior 20 to posterior 22 and medial to lateral parallel to the floor 26. Relative positions are also described as being proximal or distal where proximal is along the lower extremity toward the knee and distal is along the lower extremity toward the toes. The following examples serve to demonstrate the relative directions. The great toe is medial of the lesser toes and the fifth toe is lateral of the great toe. The toes are distal to the heel and the ankle is proximal to the toes. The instep is dorsal and the arch is plantar. The toenails are dorsal and distal on the toes.

Figure 2:
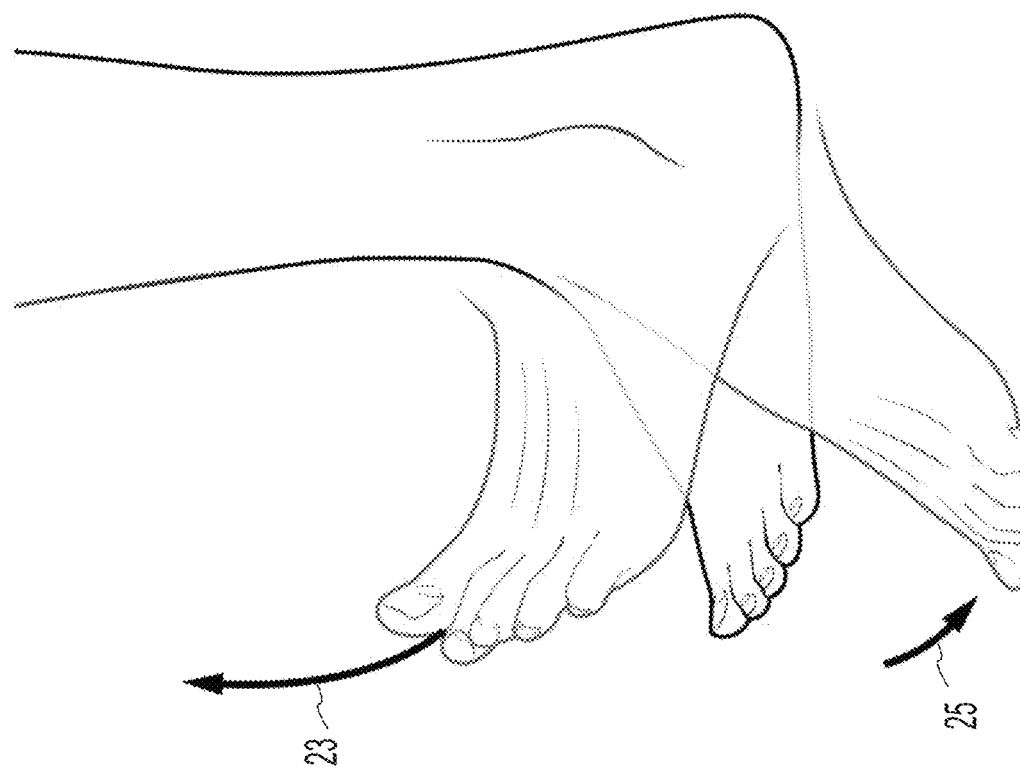
FIG. 2 is a lateral view of a foot illustrating dorsiflexion and plantar flexion.

FIG. 2 illustrates dorsiflexion 23 in which the toes are moved dorsally, or closer to the shin, by decreasing the angle between the dorsum of the foot and the leg and plantar flexion 25 in which the toes are moved plantar, or further away from the shin, by increasing the angle between the dorsum of the foot and the leg. For example when one walks on their heels, the ankle is dorsiflexed and when one walks on their toes, the ankle is plantar flexed.

Figure 3:
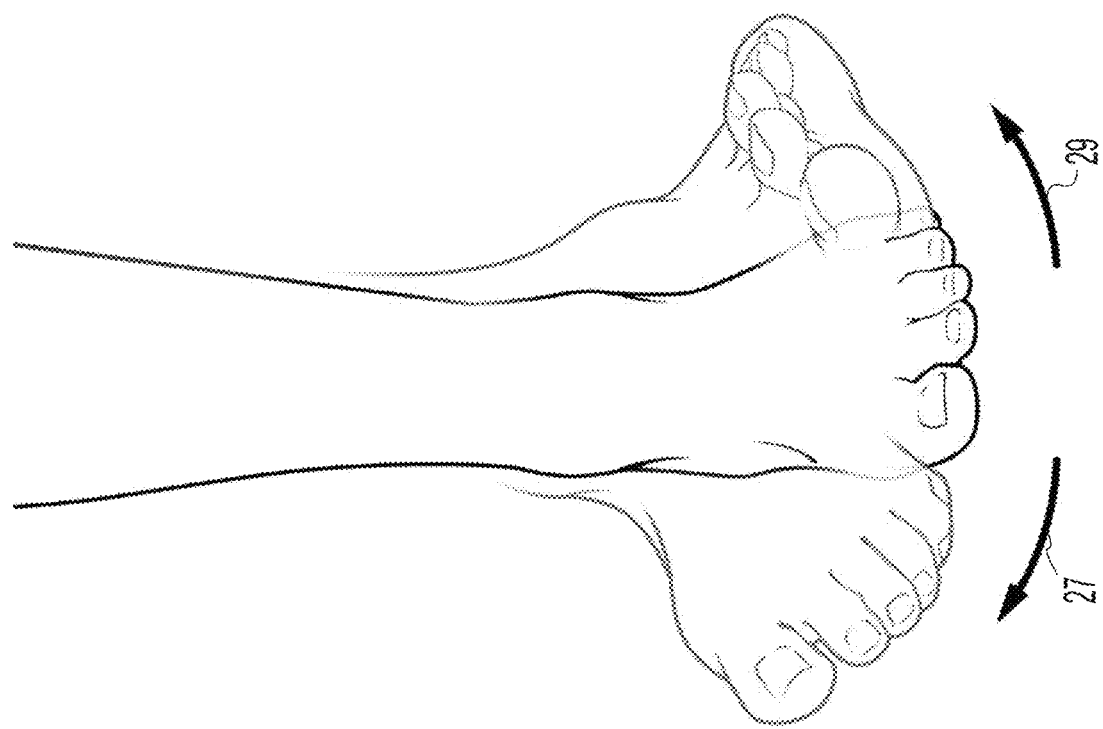
FIG. 3 is a coronal view of a foot illustrating inversion and eversion.

FIG. 3 illustrates inversion 27 in which the sole of the foot is tilted toward the sagittal plane or midline of the body and eversion 29 in which the sole of the foot is tilted away from the sagittal plane.

FIGS. 4-10 illustrate the arrangement of the bones within the foot 30. A right foot is illustrated. Beginning at the proximal example of the foot, the heel bone or calcaneus 32 projects plantar. The talus 34 is dorsal to the calcaneus 32 and articulates with it at the talocalcaneal or subtalar joint. Dorsally, the talus articulates medially with the tibia 36 and laterally with the fibula 38 at the ankle joint. Distal to the ankle are the navicular bone 40 medially and the cuboid bone 42 laterally which articulate with the talus and calcaneus respectively. The navicular bone 40 and cuboid bone 42 may also articulate with one another at the lateral side of the navicular bone and the medial side of the cuboid bone. Three cuneiform bones lie distal to the navicular bone and articulate with the navicular bone and one another. The first, or medial, cuneiform 44 is located on the medial side of the foot 30. The second, or intermediate, cuneiform 46 is located lateral of the first cuneiform 44. The third, or lateral, cuneiform 48 is located lateral of the second cuneiform 46. The third cuneiform 48 also articulates with the cuboid bone 42. Five metatarsals 50, 52, 54, 56, 58 extend distally from and articulate with the cuneiform and cuboid bones. The metatarsals are numbered from 1 to 5 starting with the first metatarsal 50 on the medial side of the foot and ending with the fifth metatarsal 58 on the lateral side of the foot 30. The first metatarsal 50 articulates with the first cuneiform 44 at a metatarsocuneiform (MTC) joint 51. The second metatarsal 52 articulates with the first, second and third cuneiforms 44, 46, 48 and may articulate with the first metatarsal as well. Five proximal phalanges 60, 62, 64, 66, 68 extend distally from and articulate with the five metatarsals respectively. The first proximal phalanx 60 articulates with the first metatarsal 50 at a metatarsophalangeal (MTP) joint 61. One or more distal phalanges 70, 72, 74, 76, 78, 80 extend distally from the proximal phalanges. The first metatarsal 50, first proximal phalanx 60, and, first distal phalanx 70 together are referred to as the first ray of the foot. Similarly, the metatarsal, proximal phalanx, and distal phalanges corresponding to the lesser digits are referred to as the second through fifth rays respectively.

Figure 5:
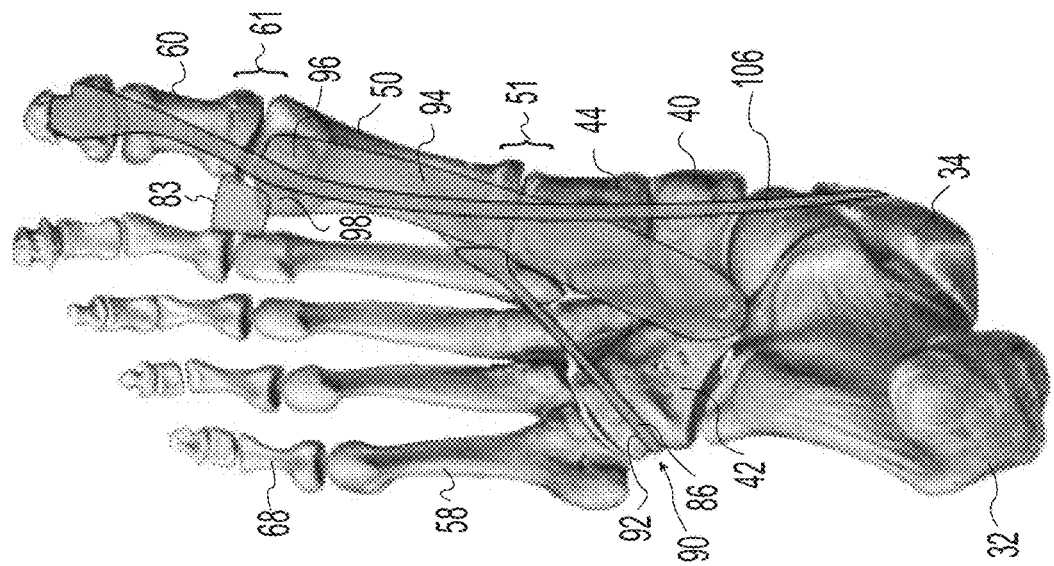
FIG. 5 is a plantar view illustrating bones, tendons, and ligaments of the foot.
Figure 4:
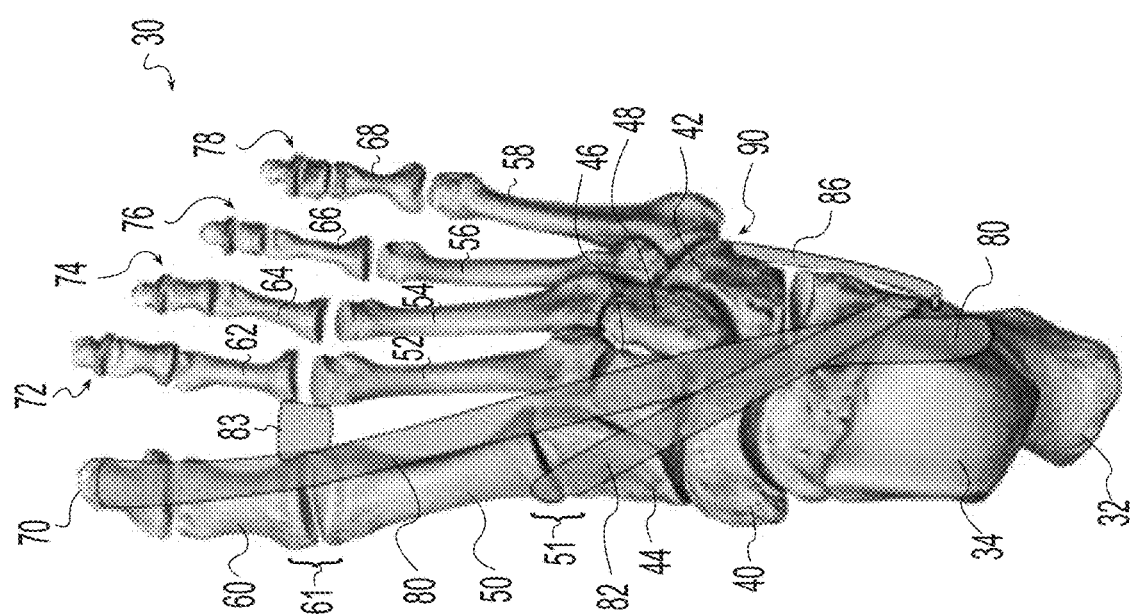
FIG. 4 is a dorsal view illustrating bones, tendons, and ligaments of the foot.
Figure 6:
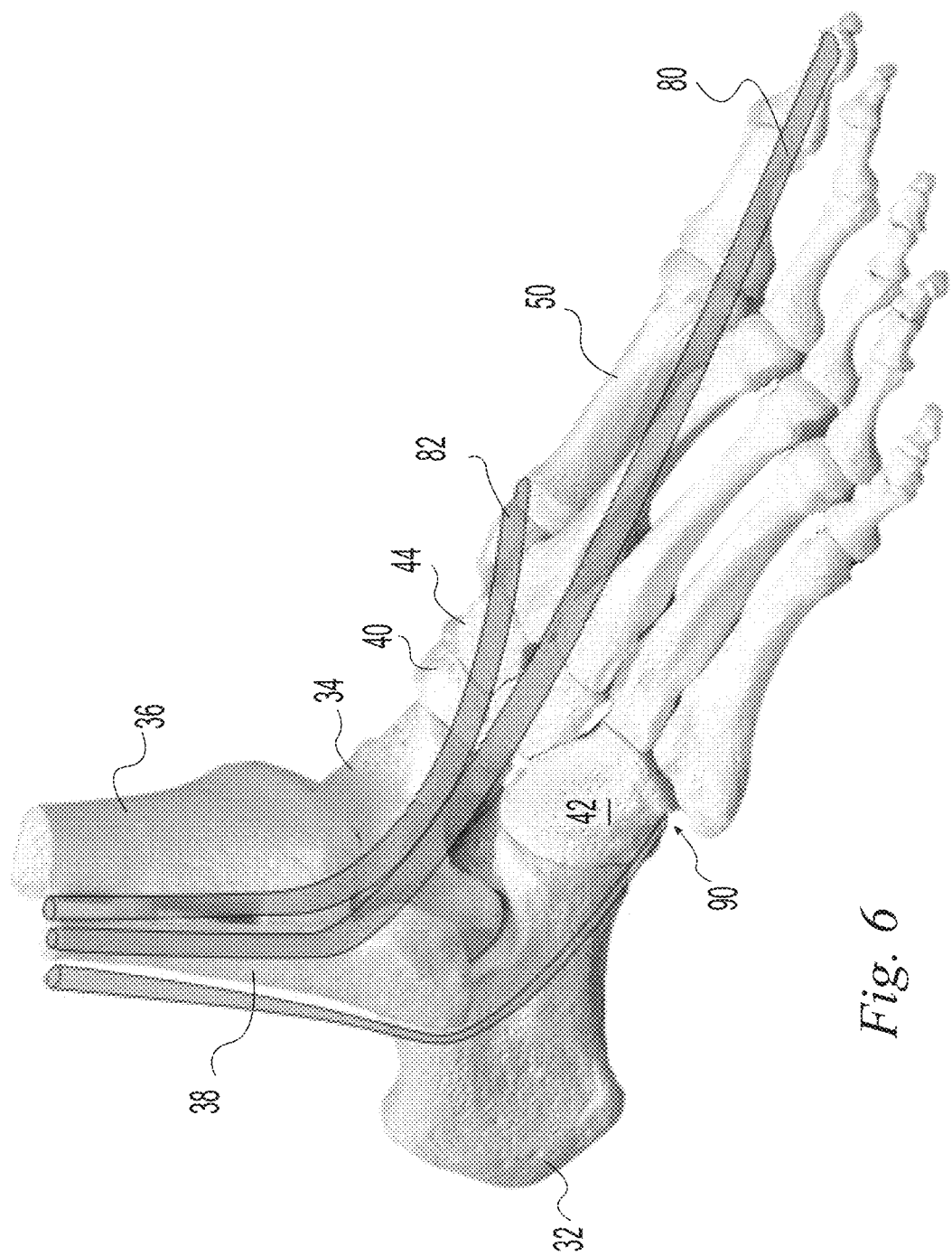
FIG. 6 is a perspective view illustrating bones, tendons, and ligaments of the foot.
Figure 9:
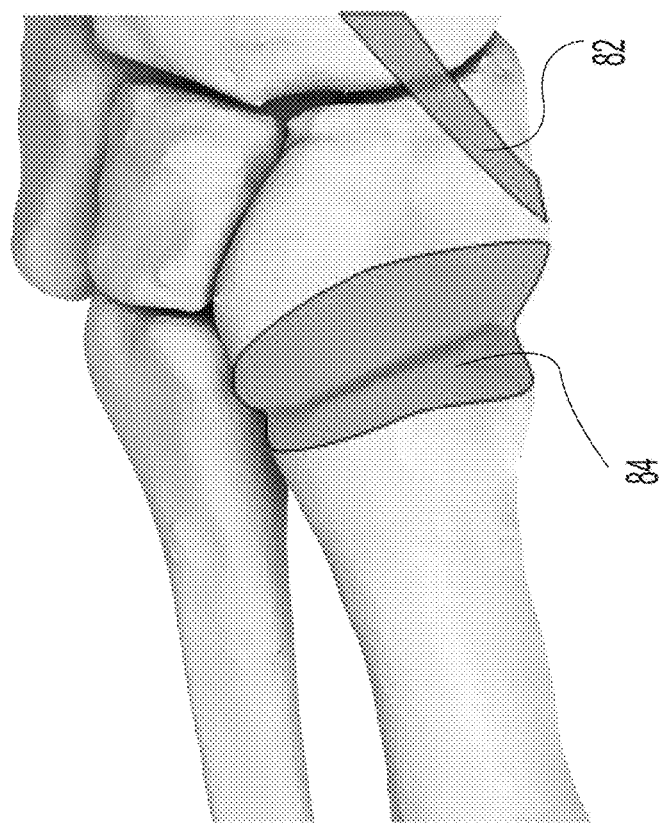
FIG. 9 is a dorsal view of the MTC joint of the first ray of the foot.
Figure 10:
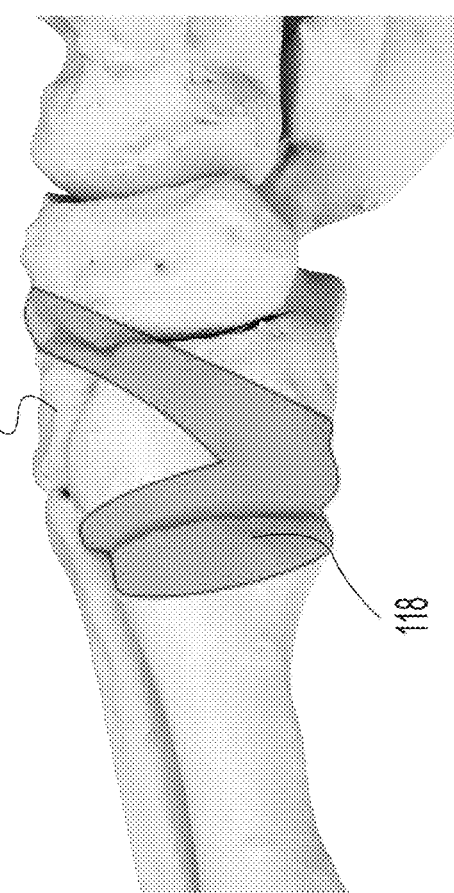
FIG. 10 is a medial view of the MTC joint of the first ray of the foot.

FIG. 4 is a dorsal view illustrating bones, tendons and ligaments of the foot. Plantar structures illustrated in FIG. 5 are omitted from FIG. 4 for clarity. The extensor hallucis longus muscle originates in the anterior portion of the leg, the extensor hallucis longus tendon 80 extends distally across the ankle and along the first ray to insert into the base of the distal phalanx 70. The tibialis anterior muscle originates in the lateral portion of the leg and the tibialis anterior tendon 82 extends distally across the ankle and inserts into the first cuneiform 44 and first metatarsus 50 at the first MTC joint 51 where it contributes to the MTC capsular structure 84 (FIGS. 9 and 10). A transverse intermetatarsal ligament 83 inserts into the capsule of the MTP joint such that it connects the heads of the first through fifth metatarsal bones. In FIG. 4, only the connection between the first and second metatarsal bones 50, 52 is shown.

FIG. 5 is a plantar view illustrating bones, tendons, and ligaments of the foot. Dorsal structures shown in FIG. 4 are omitted from FIG. 5 for clarity. The peroneus longus muscle originates at the head of the fibula and its tendon 86 passes posteriorly around the lateral malleolus 88 of the ankle, around the cuboid notch 90 on the lateral side of the cuboid bone 42, along the peroneal sulcus 92 on the plantar surface of the cuboid bone 42, and inserts into the first metatarsal 50. The flexor hallucis brevis muscle 94 originates from the cuboid 42 and third cuneiform 48 and divides distally where it inserts into the base of the proximal phalanx 60. Medial and lateral sesamoid bones 96, 98 are present in each portion of the divided tendon at the MTP joint 61. The sesamoids 96, 98 articulate with the planar surface of the metatarsal head in two grooves 100, 102 separated by a rounded ridge, or crista 104 (FIG. 8). The flexor hallucis longus muscle originates from the posterior portion of the fibula 38. The flexor hallucis longus tendon 106 crosses the posterior surface of the lower end of the tibia, the posterior surface of the talus, runs forward between the two heads of the flexor hallucis brevis 94, and is inserted into the base of the distal phalanx 70 of the great toe.

FIG. 7 is a medial view of tendons at the MTP joint 61 of the first ray. A medial collateral ligament 108 originates from the head of the first metatarsus 50 and inserts into the proximal phalanx 60. A medial metatarsosesamoid ligament 110 originates from the head of the first metatarsus 50 and inserts into the medial sesamoid bone 96. Similar collateral and metatarsosesamoid ligaments are found on the lateral side of the first MTP joint. The flexor hallucis brevis 94 is shown inserting into the sesamoids 96, 98. Ligamentous fibers extend further distally in the form of a phalangealsesamoid ligament 112 from the sesamoids to the proximal phalanx 60.

FIG. 8 is a sectional view taken along line 8-8 of FIG. 7 showing the metatarsal head 50, the tendon of the extensor hallucis longus 80, the medial and lateral sesamoid bones 96, 98, the grooves 100, 102 in which the sesamoids articulate, the crista 104 separating the grooves, the flexor hallucis longus 106, the abductor hallucis 114, and the adductor hallucis 116.

FIG. 9 is a dorsal view showing the dorsal capsular structure 84 of the MTC joint 51 of the first ray including the insertion of the tibialis anterior tendon 82.

FIG. 10 is a medial view of the MTC joint 51 of the first ray showing the medial capsular structure 118.

Figure 12:
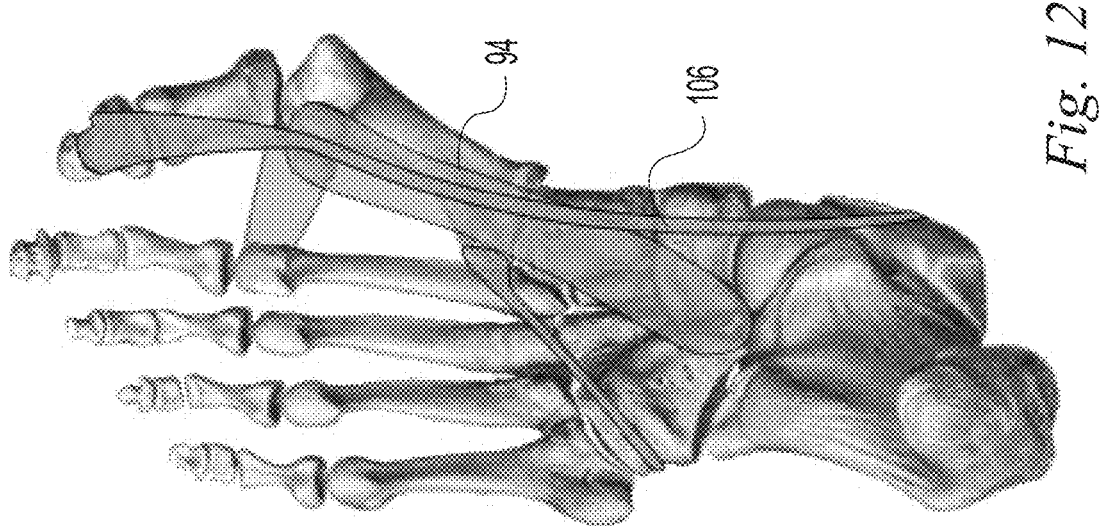
FIG. 12 is a plantar view illustrating deformity of the foot.
Figure 11:
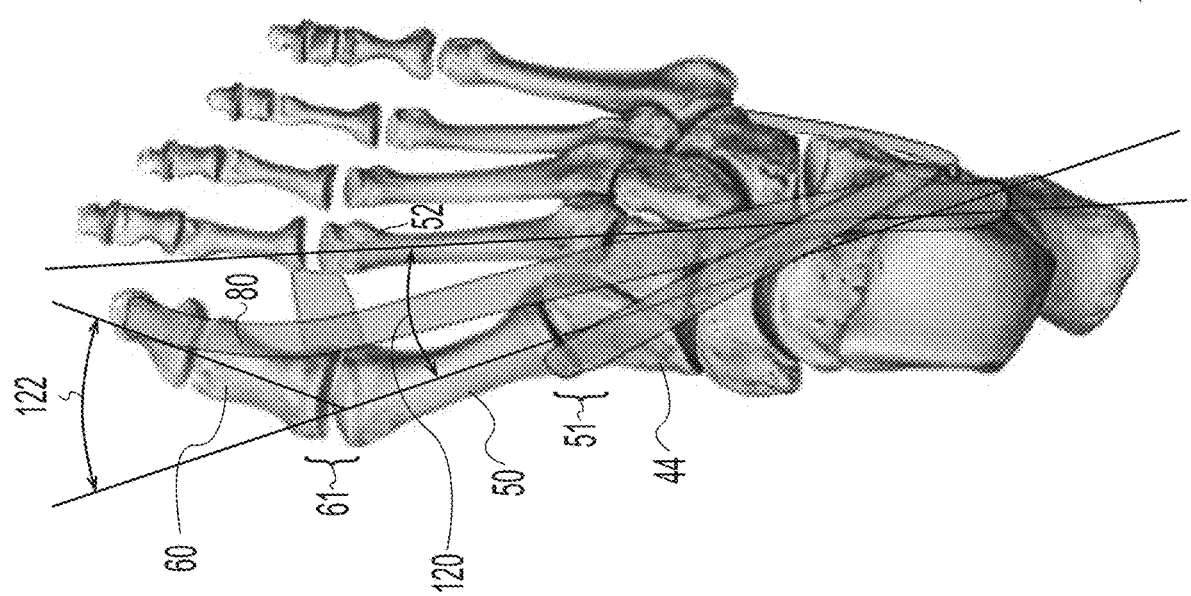
FIG. 11 is a dorsal view illustrating deformity of the foot.
Figure 13:
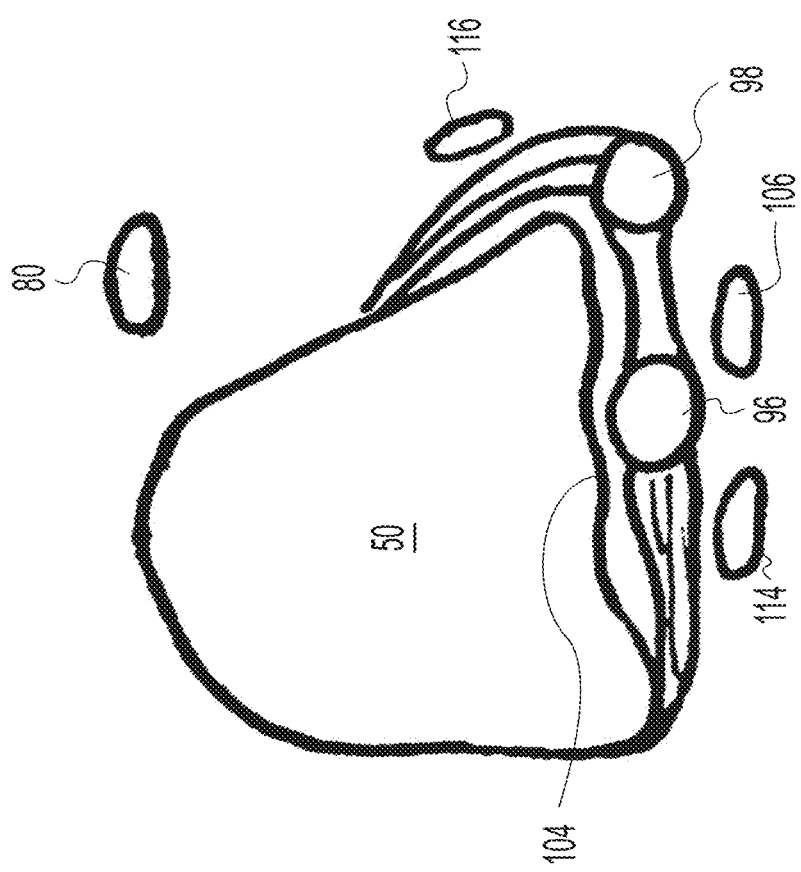
FIG. 13 is a sectional view similar to that of FIG. 8 but illustrating deformity of the foot.
Figure 16:
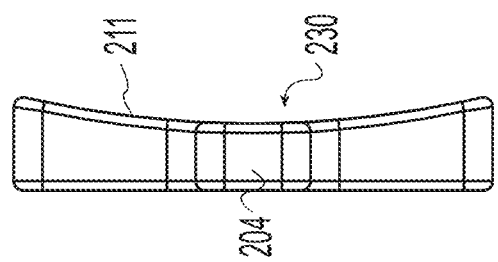
FIG. 16 is a side elevation view of the osteotomy guide of FIG. 14.
Figure 15:
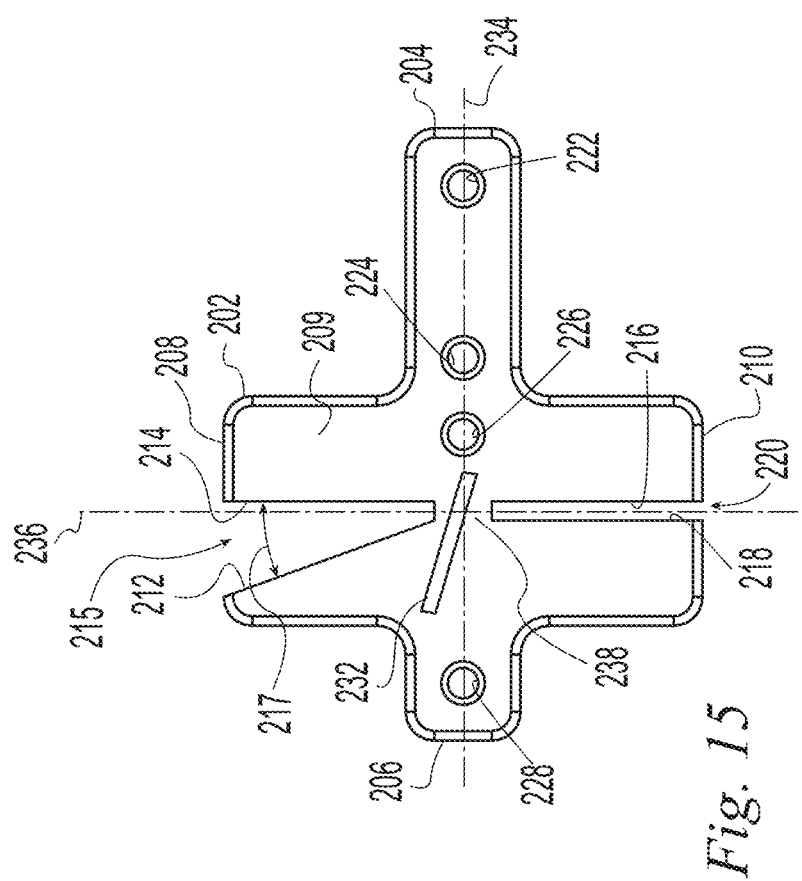
FIG. 15 is a top plan view of the osteotomy guide of FIG. 14.
Figure 17:
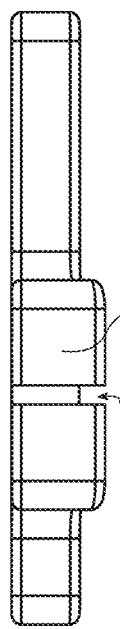
FIG. 17 is a front elevation view of the osteotomy guide of FIG. 14.

FIGS. 11-13 illustrate deformities of the first ray. In a dorsal view, as shown in FIG. 11, an intermetatarsal angle (IMA) 120 may be measured between the longitudinal axes of the first and second metatarsal bones 50, 52. The angle is considered abnormal when it is 9 degrees or greater and the condition is known as metatarsus primus varus (MPV) deformity. A mild deformity is less than 12 degrees, a moderate deformity is 12-15 degrees, and a severe deformity is greater than 15 degrees. Similarly, a hallux valgus angle (HVA) 122 may be measured between the longitudinal axes of the first metatarsus 50 and the first proximal phalanx 60 at the MTP joint 61. The angle is considered abnormal when it is 15 degrees or greater and the condition is known as a hallux valgus (HV) deformity. A mild deformity is less than 20 degrees, a moderate deformity is 20 to 40 degrees, and a severe deformity is greater than 40 degrees.

MPV and HV often occur together as shown in FIGS. 11-12. As the deformities progress several changes may occur in and around the MTC and MTP joints. Referring to FIG. 13, as the IMA and HVA increase, the extensors 80, flexors 106, abductors 114, and adductors 116 of the first ray (along with the sesamoids 96, 98) are shifted laterally relative to the MTP joint. The laterally shifted tendons exert tension lateral to the MTP joint creating a bow string effect (as best seen in FIGS. 11 and 12) that tends to cause the deformities to increase. The lateral shift of the sesamoids 96, 98 is often accompanied by erosion of the crista. The abnormal muscle forces cause the metatarsus 50 to pronate, or in other words, rotate so that the dorsal example of the bone moves medially and the plantar example moves laterally. Rotation in the opposite direction is referred to as supination. Soft tissues on the medial side of the MTP joint and lateral side of the MTC joint attenuate, through lengthening and thinning, thus weakening the capsule and permitting the deformities to progress. Soft tissues on the opposite sides of the capsule tend to shorten, thicken and form contractures making it difficult to reduce the joints to their normal angular alignment.

More generally, deformities of the first ray may include metatarsus primus varus, hallux valgus, abnormal pronation, abnormal supination, abnormal dorsiflexion, and/or abnormal plantarflexion. These deformities correspond to three different planar rotations. Metatarsus primus varus and hallux valgus result from rotations in the transverse plane 24. Pronation and supination are rotation in the coronal plane 10. Dorsiflexion and plantar flexion are rotation in the sagittal plane.

The terms "suture" and "suture strand" are used herein to mean any strand or flexible member, natural or synthetic, able to be passed through material and useful in a surgical procedure. The term "transverse" is used herein to mean crossing as in non-parallel.

The present invention provides methods and devices for performing an osteotomy on a bone. FIGS. 14-17 depict an illustrative osteotomy guide 200 according to the present invention. The guide 200 includes a guide body 202 having a proximal end 204, a distal end 206, a first side 208, a second side 210 opposite the first side 208, an upper surface 4, and a lower surface 211. First and second guide surfaces 212, 214 are formed on the first side 208 of the guide body and are separated by a guide angle 217. The first and second guide surfaces 212, 214 converge from the first side 208 toward the second side 210 of the guide body and define a wedge shaped slot 215. The first and second guide surfaces are operable to guide a cutter to remove a wedge of bone from a first side of a bone. The open wedge shaped slot 215 shown in the illustrative example of FIGS. 14-17 facilitates visualization of the bone to be cut and removal of the cut bone. A third guide surface 216 is formed on the second side 210 of the guide body. The third guide surface 216 is operable to guide a cutter to make a cut on a second side of a bone. For example, in the illustrative example of FIGS. 14-17, the first, second, and third guide surfaces 212, 214, 216 include planar surfaces against which a cutter may be supported to guide the cutter to make a cut coplanar with the guide surface. In the illustrative example of FIGS. 14-17, an optional fourth guide surface 218 is provided parallel to and opposite the third guide surface 216 to further constrain a cutter. The third and fourth guide surfaces 216, 218 define a parallel slot 220 between them operable to constrain a saw blade between them to a single plane. The third and fourth guide surfaces 216, 218 are spaced apart so that slot 220 receives a cutter, e.g. a saw blade, in planar sliding relationship. Similarly, rather than forming an open wedge, the first and second guide surfaces 212, 214 may be opposed by fifth and sixth guide surfaces to define narrow slots separated by the guide angle 217 and able to receive a cutter in planar sliding relationship. The guide surfaces 212, 214, 216 converge toward the center of the guide 200 but are spaced apart at the center by a solid portion 238. The solid portion 238 of the guide acts as a cutter stop to prevent a cutter from cutting all the way through the bone so that a central portion of the bone is preserved to act as a hinge about which the bone may be rotated.

The guide body 202 includes one or more fixation elements for attaching the guide to a bone to be cut. In the illustrative example of FIGS. 14-17, a plurality of fixation elements are provided with at least one fixation element proximal to the guide surfaces and at least one fixation element distal to the guide surfaces. In the illustrative example of FIGS. 14-17, the fixation elements are in the form of holes 222, 224, 226, 228 through the guide body 202 from the upper surface 209 to the lower surface 211 and operable to receive pins, nails, screws or other suitable fasteners to attach the guide body 202 to a bone. In the illustrative example of FIGS. 14-17, three holes 222, 224, 226 are provided proximal to the guide surfaces 212, 214, 216 and one hole 228 is provided distal to the guide surfaces.

The lower surface 211 of the guide body 202 is curved to form a concave profile 230 to engage a curved outer surface of a bone. In the illustrative example of FIGS. 14-17, the third guide surface 216 is coplanar with the second guide surface 214 to aid in producing a bone wedge that will better fit the opposite side of the bone as will be explained in more detail below. The guide surfaces 212, 214, 216 guide a cutter to make cuts that converge toward the center of the guide 200 from each of the first and second sides 208, 210 but stop short of meeting and completely bisecting the bone. This leaves a portion of bone intact toward the center of the bone.

A reference mark 232 is provided to indicate the amount of angular correction that the guide 200 will produce. The reference mark 232 is angled relative to a first, longitudinal axis 234 of the guide by the same amount as the first guide surface 212 is angled relative to a second axis 236 perpendicular to the first axis 234. In the illustrative example of FIGS. 14-17, the first axis 234 extends proximodistally and the fixation holes 222, 224, 226, and 228 are aligned on the first axis 234. The second axis 236 is perpendicular to the first axis 234 and extends between the first and second sides 208, 210.

The osteotomy guide 200 may include a set of two or more osteotomy guides, each of which has a different guide angle 217. The osteotomy guide 200 may include guides with mirrored guide surface positions. For example, on one osteotomy guide, the first and second guide surfaces 212, 214 may form a wedge on the first side 208 of the guide (as shown) while on another guide, the first and second guide surface may form a wedge on the second side 210 of the guide. For example, a right guide may be provided for cutting a bone on the right side of a patient's body and a mirrored left guide may be provided for cutting a bone on the left side of a patient's body. For example, an osteotomy guide for guiding the formation of an osteotomy for correcting an MPV deformity of the first ray of a human foot may be provided in a right configuration with the wedge producing first and second guide surfaces 212, 214 on the first side 208 of the guide corresponding to the lateral side of a right foot metatarsus and a left configuration with the wedge producing first and second guide surfaces 212, 214 on the second side 210 of the guide corresponding to the lateral side of a left foot metatarsus. Alternatively, the guide may have sufficient symmetry to allow it to be rotated 180 degrees for use on a left or right bone.

FIGS. 18-22 illustrate a method of performing an osteotomy on a bone. While the osteotomy guide of FIGS. 14-17 is well suited to performing the illustrative osteotomy, the osteotomy may be performed using another guide or no guide at all with the cuts being made freehand. However, the illustrative method will be described being performed with the illustrative guide of FIGS. 14-17 along with advantages that result from using such a guide.

In an illustrative method according to the present invention, a portion of bone is removed from a first side of a bone to create a gap on the first side of the bone. A cut is made on a second side of the bone, opposite the first side. The bone is rotated from a first, initial position in which the bone was cut to a second position to close the gap on the first side of the bone and open the cut on the second side of the bone to create a gap on the second side of the bone. The bone may be cut through such that the cuts on opposite sides of the bone meet. Alternatively, the cuts may stop short of meeting so that a portion of bone remains connecting the proximal and distal bone portions and about which the bone may rotate or bend. The bone may be fixed in the second position to heal. The gap on the second side of the bone may be filled to facilitate bone healing. For example, the gap may be filled with a filler including autograft tissue, allograft tissue, xenograft tissue, plastic, metal, or ceramic. The portion of bone removed from the first side of the bone may be used to fill the gap created on the second side of the bone to facilitate bone healing. For example, a wedge of bone may be removed from the first side of the bone and inserted into a wedge shaped gap formed on the second side of the bone when the bone is rotated.

The bone may be secured in the second position with a fixation element such as, for example, a plate, pin, screw, or other fixation element.

In the illustrative method of FIGS. 18-22, an osteotomy guide 200 is positioned over a bone to be cut. In the illustrative method of FIGS. 18-22, the bone is a first metatarsus 300 of a human foot having an MIN angular deformity. The osteotomy guide 200 is selected to have a guide angle 217 corresponding to a desired amount of MPV angular correction and a configuration appropriate for the operative side of the body. In the illustrative example of FIGS. 18-22, the deformity is on a right foot so it is desirable to move the distal end of the metatarsus 300 laterally. Therefore, a guide 200 is selected with the wedge producing first and second guide surfaces 212, 214 on the first or lateral side 208 of the guide. One or more pins, screw, nails, or other fixation members are inserted through the osteotomy guide 200 and into the bone to secure the osteotomy guide 200 to the bone. In the illustrative example of FIGS. 18-22, two pins 302, 304 are inserted through two holes 224, 226 in the proximal portion of the osteotomy guide 200 proximal to the guide surfaces. The pins secure the osteotomy guide 200 to the metatarsus 300. Utilizing two pins and two holes advantageously constrains the osteotomy guide 200 rotationally relative to the metatarsus 300. An additional pin may be placed in hole 222 to attach the osteotomy guide 200 to the first cuneiform bone 306.

Figure 19:
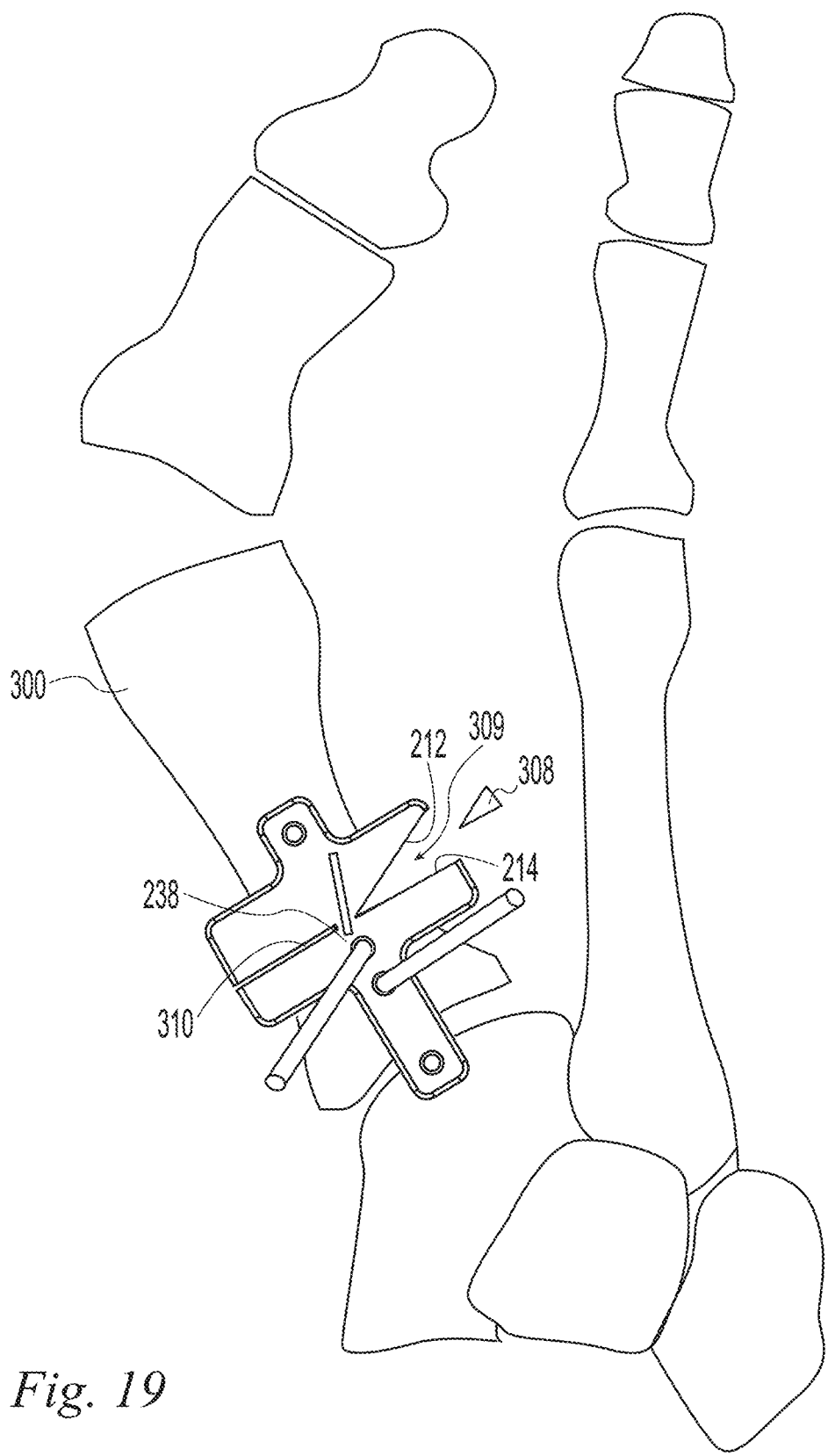

Referring to FIG. 19, a cutter is guided by first and second guide surfaces 212, 214 to remove a wedge 308 of bone from the lateral side of the metatarsus 300 leaving a lateral gap 309 and to make a cut 310 on the medial side of the metatarsus.

Figure 20:
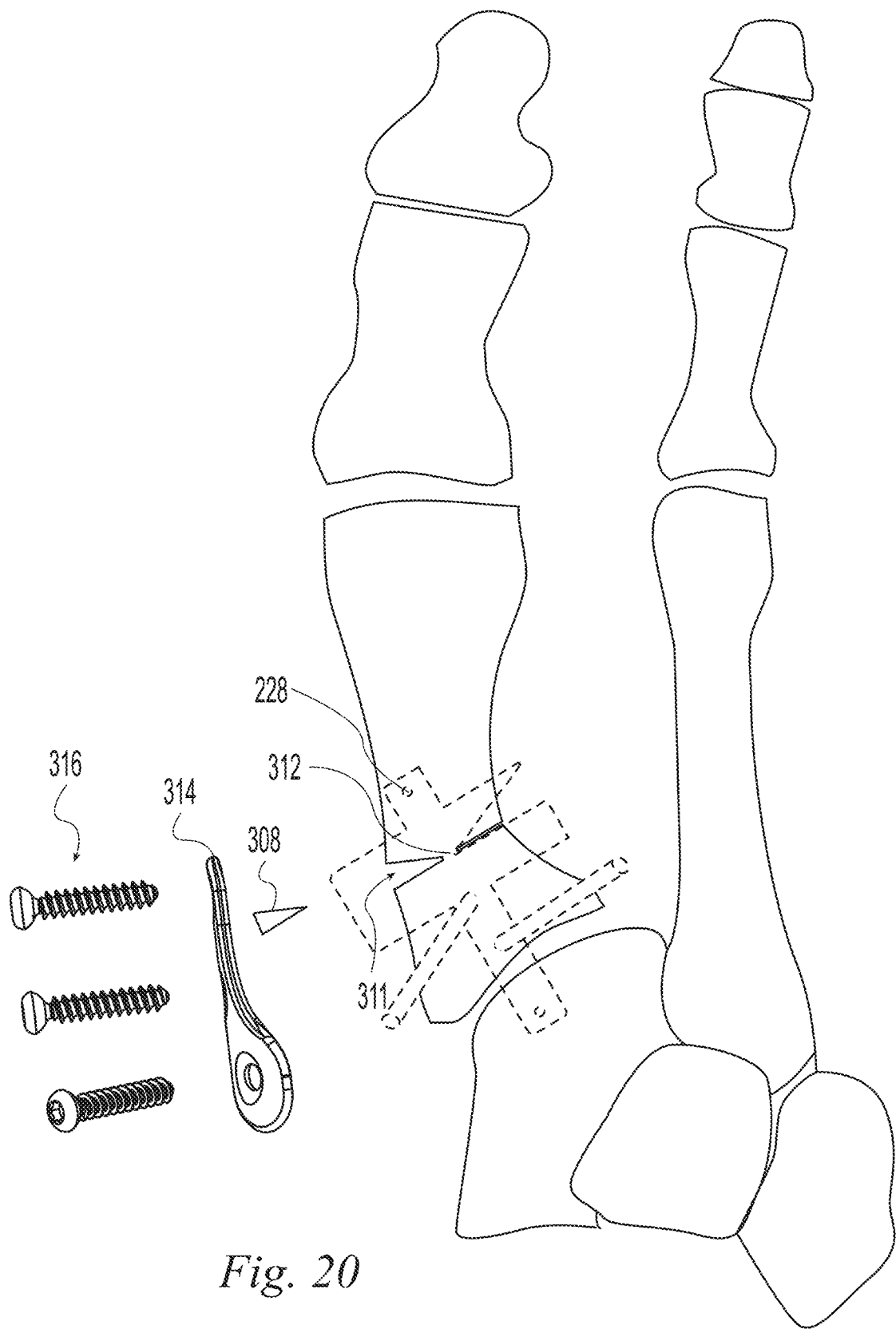
Figure 21:
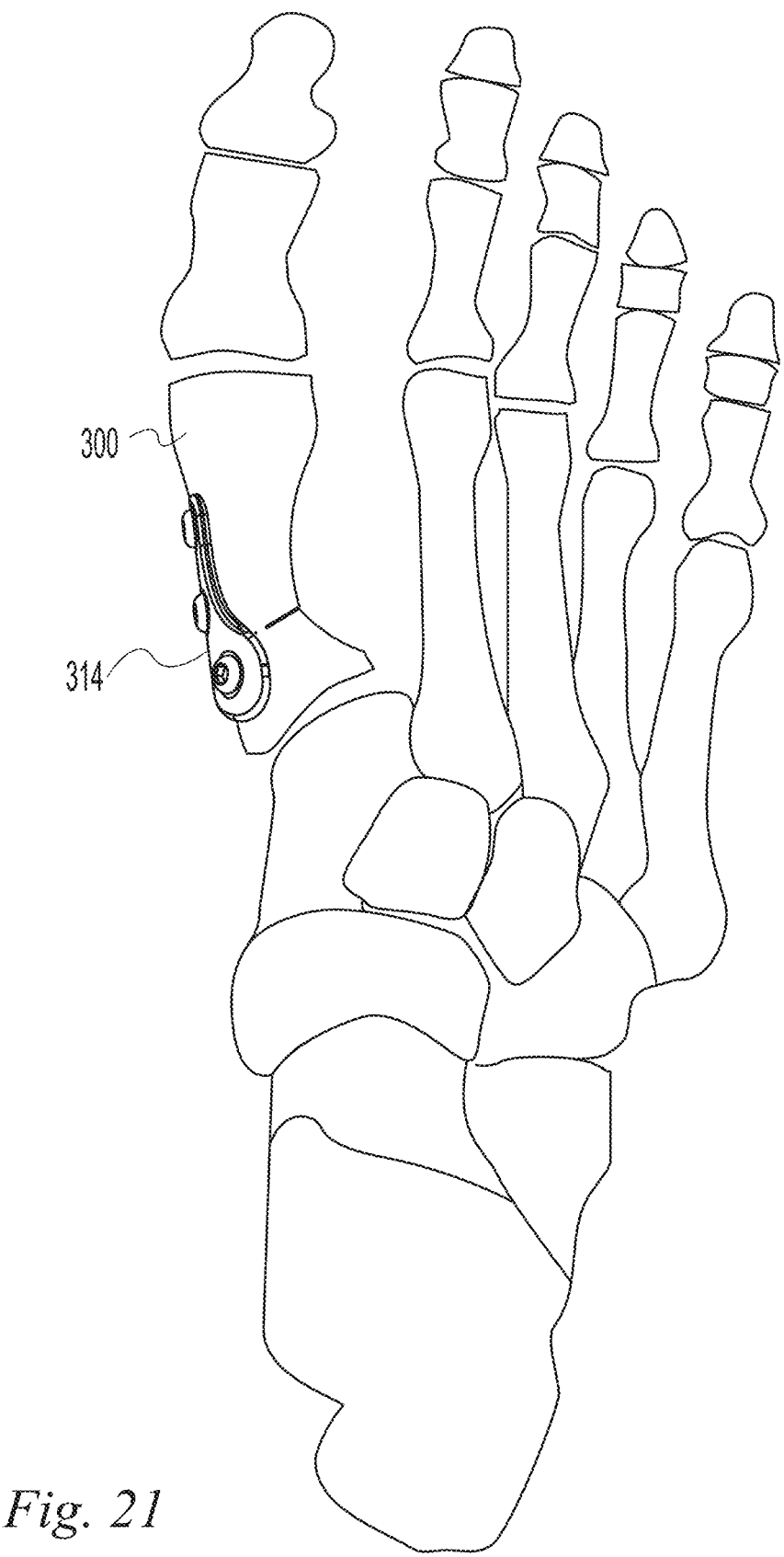
Figure 22:
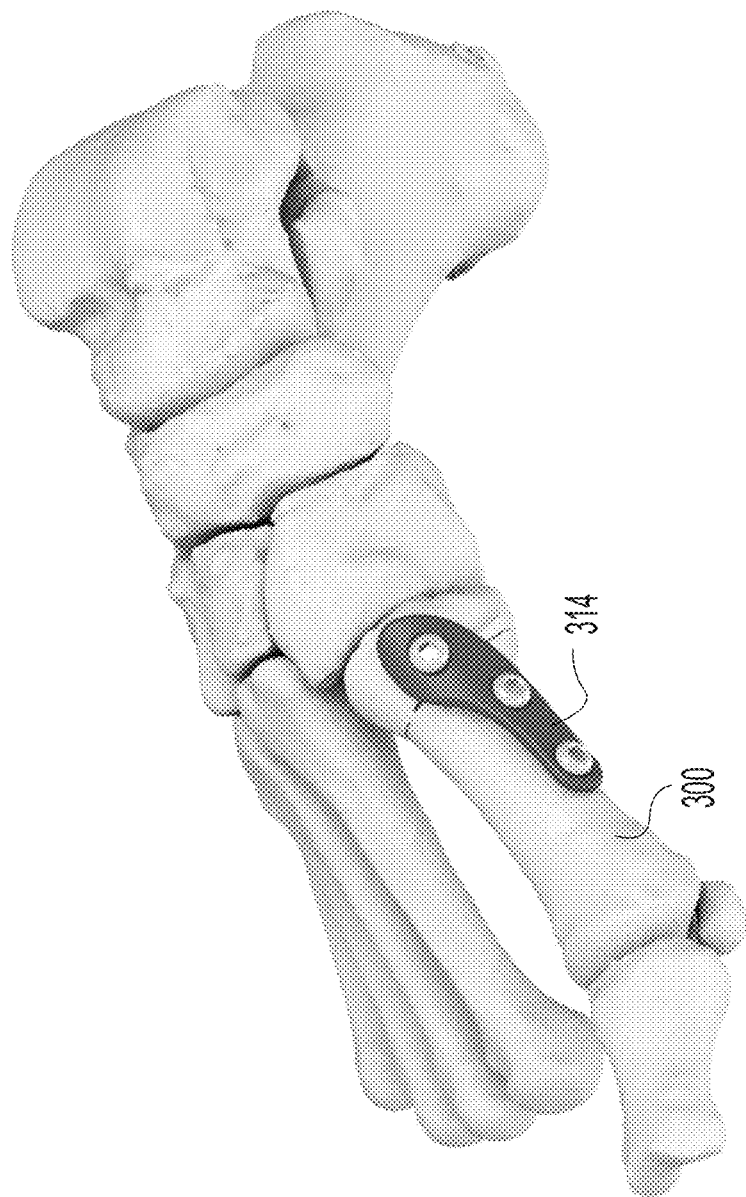
FIG. 22 is a medial view of the corrected deformity.
Figure 23:
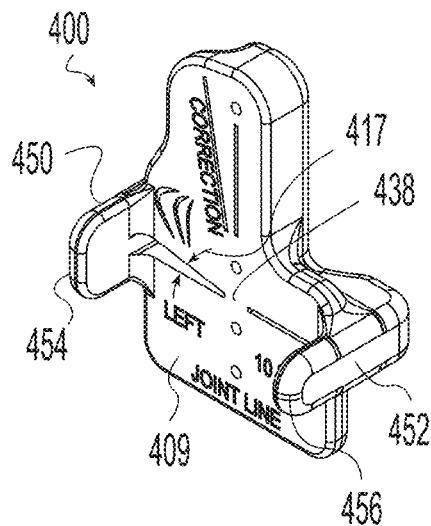
FIG. 23 is an isometric view showing the top of an osteotomy guide according to the present invention.
Figure 27:
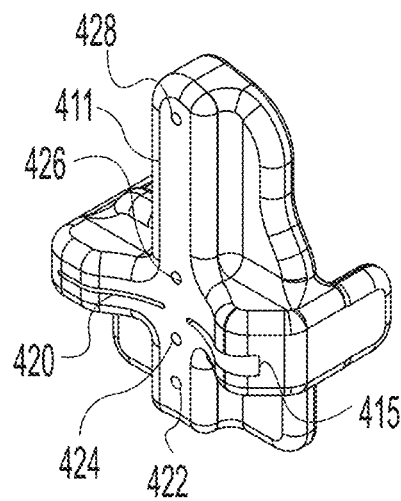
FIG. 27 is an isometric view showing the bottom of the osteotomy guide of FIG. 23.
Figure 24:
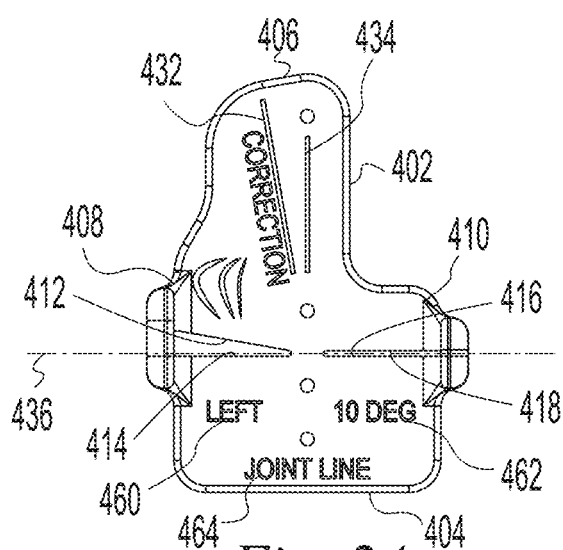
FIG. 24 is a top plan view of the osteotomy guide of FIG. 23.
Figure 26:
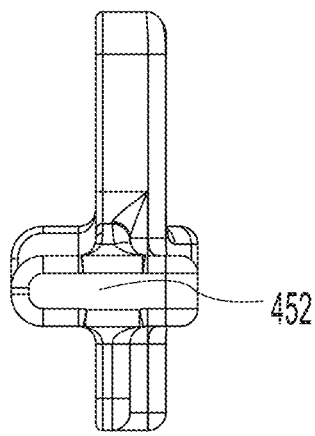
FIG. 26 is a side elevation view of the osteotomy guide of FIG. 23.
Figure 25:
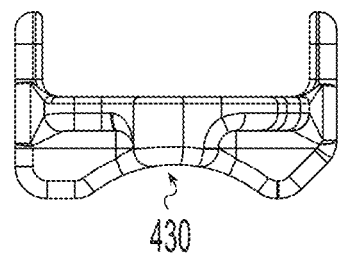
FIG. 25 is a front elevation view of the osteotomy guide of FIG. 23.

The central solid portion 238 of the guide prevents the cuts from the medial and lateral sides from meeting so that a portion of bone 312 is preserved as seen in FIG. 20. The distal portion of the metatarsus is rotated about the portion of bone 312 to close the lateral gap 309 and open the cut 310 on the medial side creating a medial gap 311. The wedge 308 from the lateral side is inserted into the medial gap 311. The bone is supported for healing with a plate 314 and screws 316. Optionally, a fixation member may be placed through the distal fixation hole 228 in the guide after the bone is rotated to support the bone in the rotated position to facilitate grafting the medial gap and placing the plate 314 and screws 316. The completed correction is shown in FIGS. 21 and 22.

Figure 14:
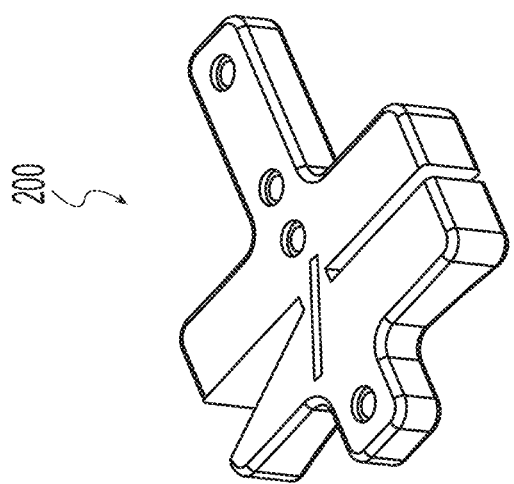
FIG. 14 is an isometric view of an osteotomy guide according to the present invention.
Figure 18:
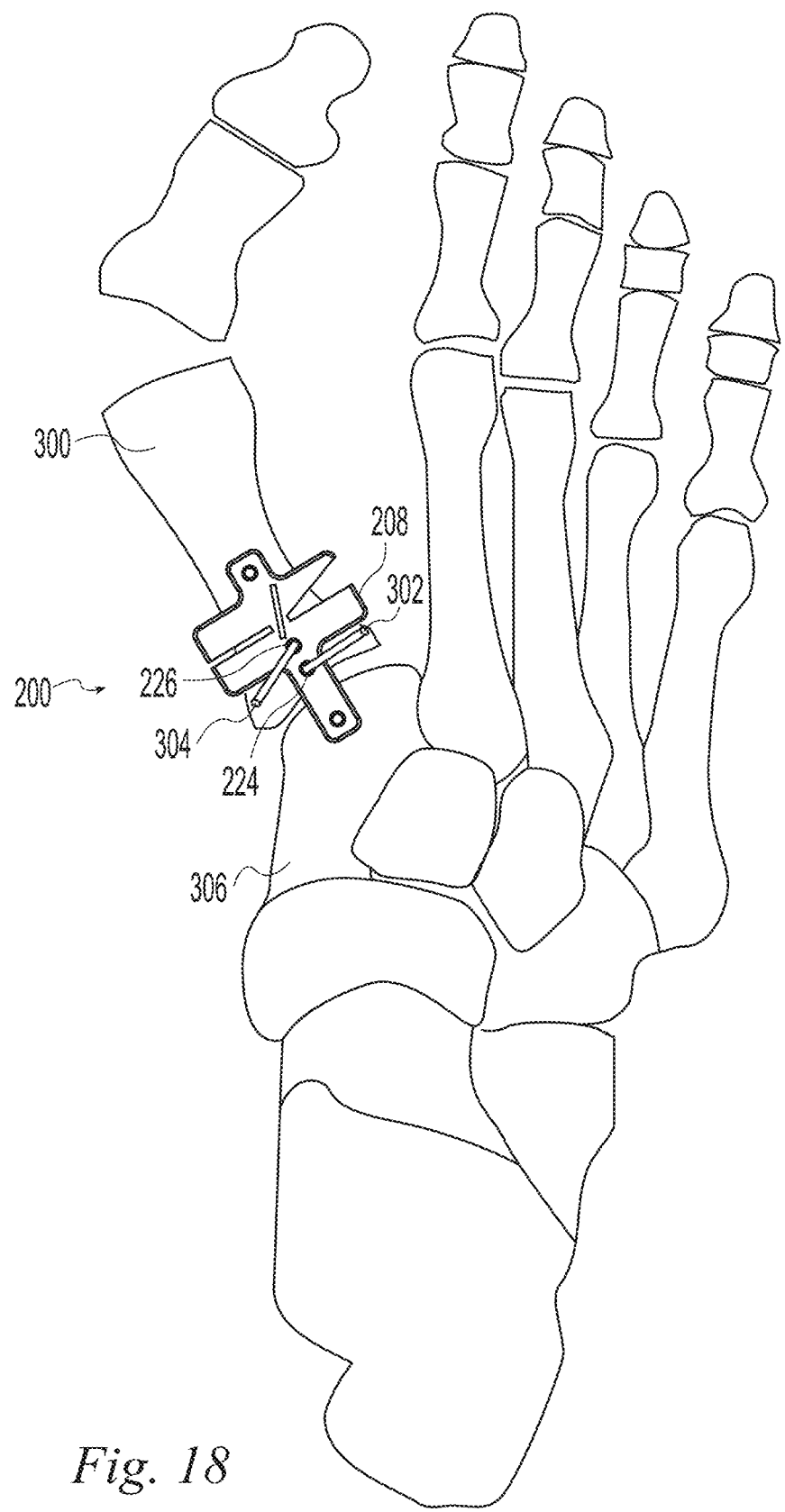
FIGS. 18-21 are dorsal views illustrating the use of the osteotomy guide of FIG. 14 to correct a deformity.

FIGS. 23-27 depict another example of an illustrative osteotomy guide 400 configured generally like that of FIG. 14. The guide 400 includes a guide body 402 having a proximal end 404, a distal end 406, a first side 408, a second side 410 opposite the first side 408, an upper surface 409, and a lower surface 411. First and second guide surfaces 412, 414 are formed on the first side 408 of the guide body and are separated by a guide angle 417. The first and second guide surfaces 412, 414 converge from the first side 408 toward the second side 410 of the guide body and define a wedge shaped slot 415. A third guide surface 416 is formed on the second side 410 of the guide body. In the illustrative example of FIGS. 23-27, an optional fourth guide surface 418 is provided parallel to and opposite the third guide surface 416. The third and fourth guide surfaces 416, 418 define a parallel slot 420 between them operable to constrain a saw blade between them. The guide surfaces 412, 414, 416 converge toward the center of the guide 400 but are spaced apart at the center by a solid portion 438.

The guide body 402 includes one or more fixation elements for attaching the guide to a bone to be cut. In the illustrative example of FIGS. 23-27, a plurality of fixation elements is provided in the form of holes 422, 424, 426, 428 through the guide body 402 from the upper surface 409 to the lower surface 411 and operable to receive pins, nails, screws or other suitable fasteners to attach the guide body 402 to a bone.

The lower surface 411 of the guide body 402 is curved to form a concave profile 430 to engage a curved outer surface of a bone.

In the illustrative example of FIGS. 23-27, first and second walls 450, 452 are provided on the first and second sides 408, 410. The first wall 450 caps the end of the wedge shaped slot 415 and the second wall 452 caps the end of the parallel slot 420. The first and second walls 450, 452 project above the upper surface 409 to terminal ends 454, 456. A saw blade guided by the one of the guide surfaces 412, 414, 416, 418 defining the slots 415, 420 is constrained to limited angles by impinging on the guide surfaces, the solid portion 438, the walls 450, 452 and terminal ends 454, 456. By adjusting the width and height of these features and the width and length of the saw blade, it is possible to protect structures surrounding the bone from being cut from accidental contact with the saw blade.

Reference marks 432, 434 are provided to indicate the amount of angular correction that the guide 400 will produce. A correction reference mark 432 is angled relative to an axial reference mark 434 by the same amount as the first guide surface 412 is angled relative to a second axis 436 perpendicular to the axial reference mark 434. The reference marks give an immediate visual indication of the amount and direction of angular correction. The correction reference mark 432 is preferably labeled "Correction" for clarity. Additional text indicators may be provided such as a direction indicator 460 and a magnitude indicator 462. For example, in the illustrative example of FIGS. 23-27, the direction indicator 460 contains the text "Left" or "Right" to indicate the direction of the correction or the side of the patient's body on which it is to be used. The magnitude indicator 462 contains text indicating the number of degrees of angular correction that the guide 400 provides. In the illustrative example of FIGS. 23-27, the guide further includes a label adjacent the proximal end 404 indicating where to position the proximal end. For example, in the illustrative example of FIGS. 23-27, the proximal end is labeled "Joint Line" to indicate that for a metatarsal corrective osteotomy, the proximal end should be positioned at the joint line of the MTC joint. In the illustrative example of FIGS. 23-27, the fixation holes 422, 424, 426, 428 are positioned to receive pins into the metatarsus with two proximal to the osteotomy cuts and two distal to the osteotomy cuts.

Figure 28:
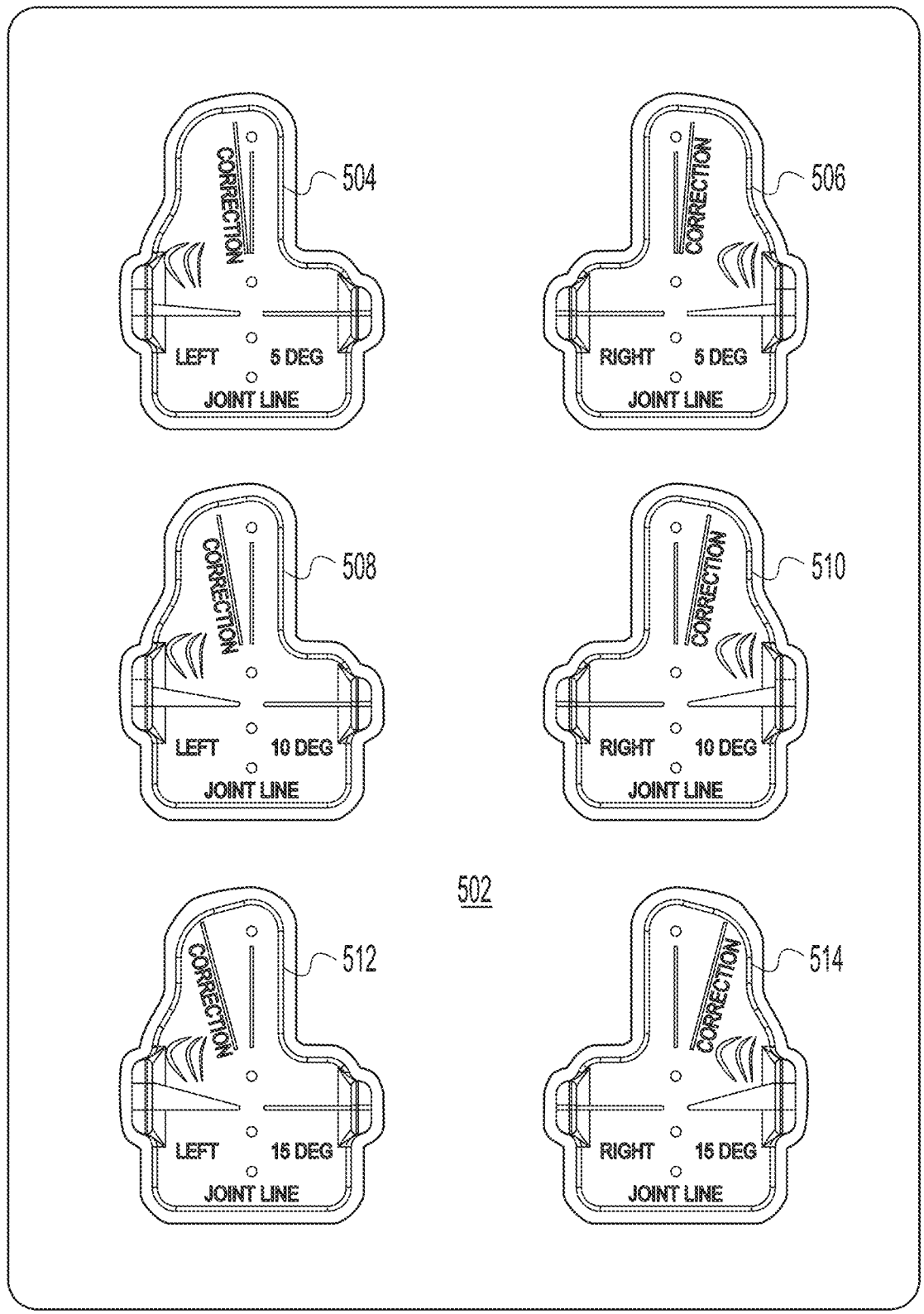
FIG. 28 is a top plan view showing a set of osteotomy guides like that of FIG. 23 having various correction angles and configured for left and right corrections.

Referring to FIG. 28, a set 500 of osteotomy guides 504, 506, 508, 510, 512, 514 are provided in a tray 502. In the illustrative example of FIG. 28, three "Left" guides 504, 508, 512 and three "Right" guides 506, 510, 514 are provided. The left guides are provided in three corrective angles corresponding to 5, 10, and 15 degrees of angular correction. The right guides are also provided with 5, 10, and 15 degrees of angular correction.

Various examples have been provided to illustrate the present invention. It will be understood that variations may be made and still be within the scope of the invention.

What is claimed is:

1. A method of performing an osteotomy on a bone, the method comprising:
    securing an osteotomy guide to the bone, the osteotomy guide comprising a proximal end, a distal end, first and second guide surfaces operable to guide a cutter to make first and second cuts on a first side of the bone, a first fixation element proximal to the guide surfaces, a second fixation element distal to the guide surfaces, and a third guide surface operable to guide a cutter to make a cut on a second side of the bone, the third guide surface extending toward but stopping short of the first and second guide surfaces, wherein the osteotomy guide is secured to the bone using one of the first and second fixation elements;
    using the osteotomy guide to guide removing a portion of bone from the first side of the bone to create a gap on the first side of the bone;
    using the osteotomy guide to guide making a cut on a second side of the bone, opposite the first side;
    rotating the bone from a first position to a second position to close the gap on the first side of the bone and open the cut on the second side of the bone to create a gap on the second side of the bone; and
    after rotating the bone from the first position to the second position, securing the osteotomy guide to the bone with the other of the first and second fixation elements to support the bone in the second position.

2. The method of claim 1 further comprising filling the gap created on the second side of the bone with a filler.

3. The method of claim 2 wherein the filler contains at least one material selected from the group consisting of autograft tissue, allograft tissue, xenograft tissue, plastic, metal, and ceramic.

4. The method of claim 2 wherein the step of filling the gap created on the second side of the bone with a filler comprises inserting at least some of the portion of bone removed from the first side of the bone into the gap on the second side of the bone.

5. The method of claim 4 wherein the step of removing a portion of bone from a first side of the bone comprises removing a wedge of bone and further wherein the step of inserting at least some of the portion of bone removed from the first side of the bone into the gap on the second side of the bone comprises inserting the wedge of bone from the first side into the gap in the second side of the bone.

6. The method of claim 1 further comprising securing the bone in the second position with a third fixation element.

7. The method of claim 6 wherein the third fixation element includes at least one element selected from the group consisting of plates, pins, and screws.

8. The method of claim 1 wherein:
    the osteotomy guide is provided as one of a set of two or more osteotomy guides,
    the first and second guide surfaces of each of the osteotomy guides comprise first and second intersecting guide surfaces spaced apart by an angle;
    the angle of at least two of the osteotomy guides are different from each other; and
    wherein the method further comprises selecting one of the osteotomy guides of the set, the selected osteotomy guide having an angle corresponding to a desired bone correction angle.

9. The method of claim 1 wherein the bone comprises a metatarsus of a first ray of a human foot.

10. The method of claim 1 wherein:
    the gap comprises a gap first end at the first side of the bone and a gap second end at a furthest extent, from the first side of the bone, at which the bone was cut to form the gap; and
    wherein the cut comprises a cut first end at the second side of the bone and a cut second end at a furthest extent, from the second side of the bone, at which the bone was cut to form the cut; and
    wherein the cut second end is further from the first side of the bone than the gap second end.

11. The method of claim 1 wherein:
    the gap defines at least a first planar surface of the bone; and
    the cut is coplanar with the first planar surface.

12. The method of claim 1 wherein removing a portion of bone from a first side of the bone comprises making a cut into the bone from the first side of the bone toward the second side of the bone and wherein making a cut on a second side of the bone comprises making a cut into the bone from the second side of the bone toward the first side of the bone, the method further comprising leaving a portion of uncut bone between the first and second sides about which the bone can rotate.

13. The method of claim 1 wherein the third guide surface is coplanar with one of the first and second guide surfaces.

14. A method of performing an osteotomy on a metatarsus of a first ray of the human foot, the method comprising:
- positioning an osteotomy guide adjacent the metatarsus, the osteotomy guide comprising a proximal end, a distal end, guide surfaces for guiding a cutter, a first fixation element proximal to the guide surfaces, and a second fixation element distal to the guide surfaces;
- securing the osteotomy guide to the metatarsus with one of the first and second fixation elements;
- guiding a cutter with the osteotomy guide to remove a portion of bone from a first side of the metatarsus to create a gap on the first side of the metatarsus;
- guiding a cutter with the osteotomy guide to make a cut on a second side of the metatarsus, opposite the first side;
- rotating the metatarsus from a first position to a second position to close the gap on the first side of the metatarsus and open the cut on the second side of the metatarsus to create a gap on the second side of the metatarsus;
- securing the osteotomy guide to the metatarsus with the other of the first and second fixation elements to support the metatarsus in the second position; and
- filling the gap created on the second side of the metatarsus.

15. The method of claim 14 wherein guiding a cutter with the osteotomy guide to remove a portion of the metatarsus from a first side of the metatarsus comprises removing a wedge of the metatarsus and further wherein filling the gap on the second side of the metatarsus comprises inserting the wedge of bone from the first side into the second side of the metatarsus.

16. The method of claim 14 further comprising securing the metatarsus in the second position with a third fixation element.

17. The method of claim 14 wherein at least one of the first and second fixation elements is a hole operable to receive a member selected from the group consisting of pins, nails, and screws.

* * * * *

UNITED STATES PATENT AND TRADEMARK OFFICE
CERTIFICATE OF CORRECTION

PATENT NO. : 10,898,211 B2
APPLICATION NO. : 14/994362
DATED : January 26, 2021
INVENTOR(S) : T. Wade Fallin Page 1 of 1

It is certified that error appears in the above-identified patent and that said Letters Patent is hereby corrected as shown below:

In the Specification

Column 7, Line 55, delete "MIN" and insert --MPV--.

In the Claims

Column 12, Line 7, Claim 15, delete "the metatarsus" and insert --bone--.

Column 12, Line 11, Claim 15, delete "bone" and insert --the metatarsus--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*